(12) United States Patent
Hoshino et al.

(10) Patent No.: US 10,939,809 B2
(45) Date of Patent: Mar. 9, 2021

(54) GRASPING SECTION OF AN ENDOSCOPE

(71) Applicant: OLYMPUS CORPORATION, Hachioji (JP)

(72) Inventors: Yuki Hoshino, Sagamihara (JP); Yasuo Funakoshi, Hachioji (JP); Risako Asai, Kawagoe (JP)

(73) Assignee: OLYMPUS CORPORATION, Tokyo (JP)

( * ) Notice: Subject to any disclaimer, the term of this patent is extended or adjusted under 35 U.S.C. 154(b) by 397 days.

(21) Appl. No.: 15/899,391

(22) Filed: Feb. 20, 2018

(65) Prior Publication Data

US 2018/0168436 A1 Jun. 21, 2018

Related U.S. Application Data

(63) Continuation of application No. PCT/JP2016/073309, filed on Aug. 8, 2016.

(30) Foreign Application Priority Data

Aug. 18, 2015 (JP) .............................. JP2015-161041

(51) Int. Cl.
  *A61B 1/005* (2006.01)
  *G02B 23/24* (2006.01)
  *A61B 1/00* (2006.01)

(52) U.S. Cl.
  CPC .............. *A61B 1/0052* (2013.01); *A61B 1/00* (2013.01); *A61B 1/0055* (2013.01);
  (Continued)

(58) Field of Classification Search
  CPC .............. A61B 1/00066; A61B 1/0052; G02B 23/2476
  (Continued)

(56) References Cited

U.S. PATENT DOCUMENTS 4,979,497 A * 12/1990 Matsuura ........... A61B 1/00068
  348/65
7,214,183 B2 * 5/2007 Miyake .............. A61B 1/00039
  600/104
(Continued)

FOREIGN PATENT DOCUMENTS

JP  S56-98206 U   8/1981
JP  2007-222651 A   9/2007
(Continued)

OTHER PUBLICATIONS

Oct. 25, 2016 International Search Report issued in International Patent Application No. PCT/JP2016/073309.
(Continued)

*Primary Examiner* — John P Leubecker
(74) *Attorney, Agent, or Firm* — Oliff PLC

(57) ABSTRACT

An endoscope includes a grasp section. The grasp section includes: a first surface adjacent, in the longitudinal axis, to a surface where the bending operation knob is provided, a protruding portion radially outwardly protruding to the longitudinal axis at a position adjacent to the first surface around the longitudinal axis, a first inclined surface provided on the protruding portion at a side adjacent to the first surface and inclined to the first surface, and a second inclined surface which is provided, on the protruding portion, at a side opposite to the first inclined surface across the protruding portion, and which is inclined to the first surface.

12 Claims, 12 Drawing Sheets

(52) U.S. Cl.
CPC .......... *A61B 1/00066* (2013.01); *G02B 23/24* (2013.01); *A61B 1/00131* (2013.01)

(58) Field of Classification Search
USPC ........................................................ 600/131
See application file for complete search history.

(56) References Cited

U.S. PATENT DOCUMENTS

| | | | |
|---|---|---|---|
| 8,113,297 B2* | 2/2012 | Sakakibara | ............... B25F 5/02 |
| | | | 173/162.1 |
| 2001/0018551 A1* | 8/2001 | Komi | ................... A61B 1/0052 |
| | | | 600/131 |
| 2009/0247828 A1* | 10/2009 | Watanabe | .......... A61B 1/00032 |
| | | | 600/131 |
| 2013/0012780 A1 | 1/2013 | Nakamura et al. | |
| 2014/0100424 A1* | 4/2014 | Hoshino | ............ A61B 1/00039 |
| | | | 600/118 |
| 2014/0200513 A1 | 7/2014 | Koitabashi et al. | |
| 2016/0157699 A1* | 6/2016 | Okamoto | ............. A61B 1/0052 |
| | | | 600/146 |
| 2016/0227983 A1* | 8/2016 | Fukuda | .................... A61B 1/12 |

FOREIGN PATENT DOCUMENTS

| | | |
|---|---|---|
| JP | 1386276 S | 4/2010 |
| JP | 1470841 S | 6/2013 |
| WO | 2011/132544 A1 | 10/2011 |

OTHER PUBLICATIONS

Apr. 23, 2019 Search Report issued in European Patent Application No. 16837026.0.
Mar. 1, 2018 International Preliminary Report on Patentability issued in International Application No. PCT/JP2016/073309.

* cited by examiner

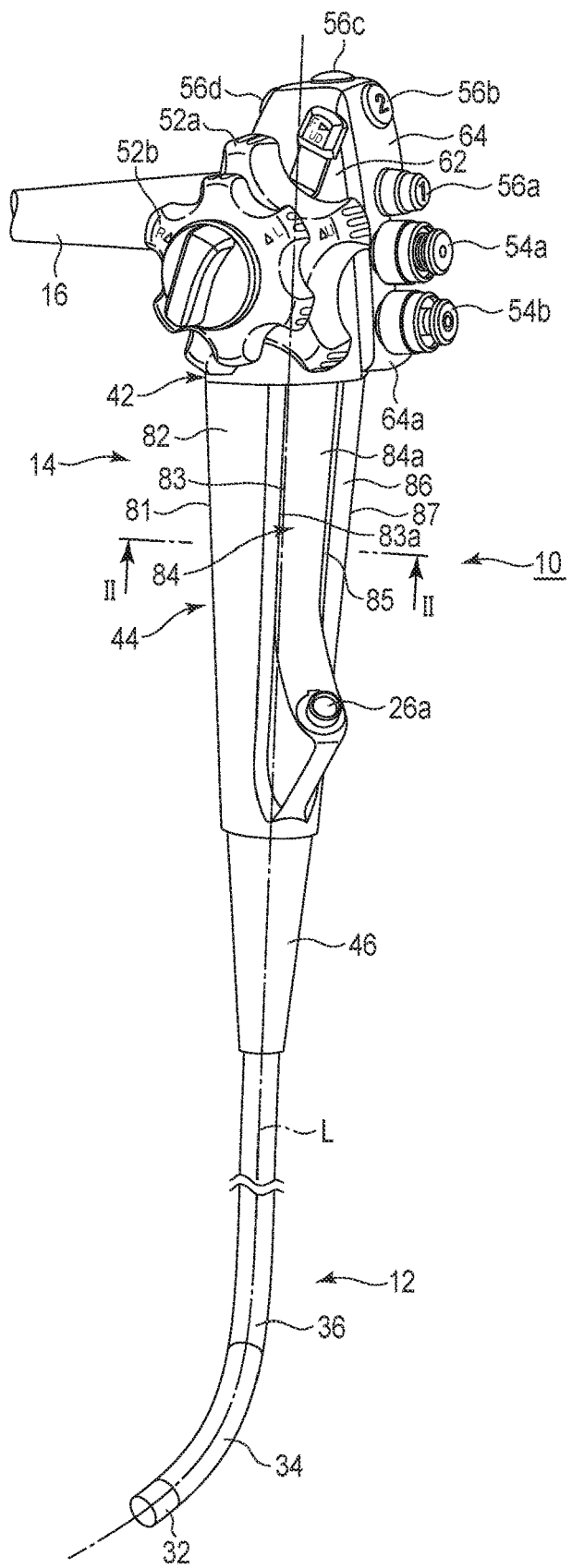
F I G. 1A

US 10,939,809 B2

GRASPING SECTION OF AN ENDOSCOPE

CROSS-REFERENCE TO RELATED APPLICATIONS

This application is a Continuation Application of PCT Application No. PCT/JP2016/073309, filed Aug. 8, 2016 and based upon and claiming the benefit of priority from prior Japanese Patent Application No. 2015-161041, filed Aug. 18, 2015, the entire contents of all of which are incorporated herein by reference.

BACKGROUND OF THE INVENTION

1. Field of the Invention

This invention relates to an endoscope which is used by grasping with a hand of a user.

2 Description of the Related Art

For example, an outer casing of a grasp section of an operation assembly of an endoscope disclosed in Jpn. Pat. Appln. KOKAI Publication No. 2007-222651 is cylindrically shaped. Two adjacent surfaces of the outer casing of the grasp section are disposed substantially at 90° to each other. Corners of these two adjacent surfaces are continuously formed in a curved surface. A ridge is formed along the longitudinal direction of the grasp section in a surface of the outer casing of the grasp section on the side where a bending operation knob is provided.

BRIEF SUMMARY OF THE INVENTION

According to one aspect of the present invention, an endoscope includes: an insertion section which is inserted into a subject and which includes a bendable bending portion and in which a longitudinal axis is defined; an operation section on which a bending operation knob is provided and is configured to remotely operate the bending portion of the insertion section; and a cylindrical grasp section which is provided between the insertion section and the operation section and which is grasped by a user, the grasp section comprising a first surface adjacent, along the longitudinal axis, to a surface formed in the operation section on a side where the bending operation knob is provided, a second surface formed on a back side of the first surface with respect to the longitudinal axis, a side surface formed between the first surface and the second surface, a protruding portion having a ridge which radially outwardly protrudes with respect to the longitudinal axis at a position adjacent to the first surface around the longitudinal axis, a first inclined surface which is provided on the protruding portion at a side adjacent to the first surface and which is inclined with respect to the first surface to be located on a back side of the second surface, and a flat or depressed second inclined surface which is provided, on the protruding portion, at a side opposite to the first inclined surface across the ridge of the protruding portion, which connects the ridge and the side surface to each other and which is inclined with respect to the first surface and the side surface.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1A is a schematic perspective view showing an endoscope according to first and second embodiments;

DETAILED DESCRIPTION OF THE INVENTION

Hereinafter, embodiments of this invention will be described with reference to the drawings.

Initially, the first embodiment is described with reference to FIG. 1A to FIG. 7A.

As shown in FIG. 1A, an endoscope 10 according to this embodiment includes an insertion section 12 to be inserted into a subject, an operation assembly 14 provided in a proximal portion of the insertion section 12, and a universal cord 16 which is provided in the operation assembly 14 and which is connected to an external device such as a controller of the endoscope 10. The universal cord 16 connects unshown external devices such as a monitor and/or the controller to the operation assembly 14. In addition, an imaginary longitudinal axis L is defined in the insertion section 12 by a distal end and a proximal end of the insertion section 12. The virtual longitudinal axis L is coaxially defined not only on the insertion section 12 but also on the operation assembly 14.

Figure 1B:
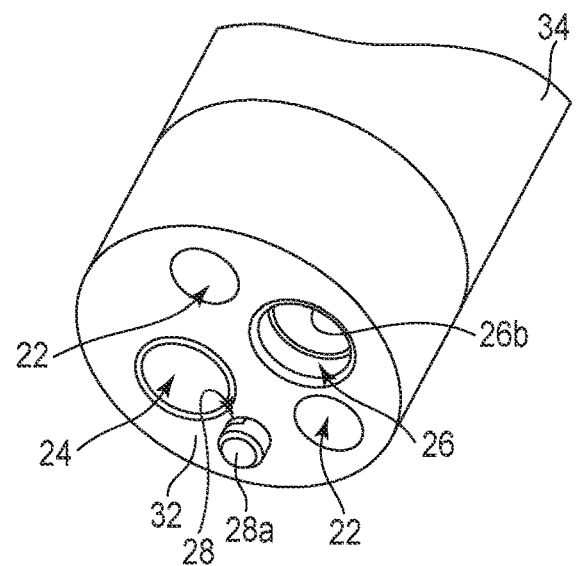
FIG. 1B is a schematic perspective view showing a distal hard portion of an insertion section of the endoscope according to the first and second embodiments.

As shown in FIG. 1A and FIG. 1B, the endoscope 10 includes an illumination optical system 22, an observation optical system 24, a treatment instrument insertion channel 26, and an air/water supply path 28, which are publicly known. The illumination optical system 22 and the observation optical system 24 are provided from a distal portion of the insertion section 12 of the endoscope 10 to an unshown connector of the universal cord 16 through the operation assembly 14. The treatment instrument insertion channel 26 has a proximal opening 26a which is an entrance for a treatment instrument in a later-described grasp section 44 of the insertion section 12, and has a distal opening 26b which is an exit for the treatment instrument in a later-described distal hard portion 32 of the insertion section 12. The distal opening 26b of the channel 26 also functions as a distal opening for a suction path. The proximal end of the suction path is provided in the unshown connector of the universal cord 16 through the operation assembly 14. The channel 26 can suck living tissues, physiological saline, and others from the distal opening 26b of the channel 26 at the distal end of the distal hard portion 32 by a press operation of a later-described suction button 54a. The air/water supply path 28 discharges, for example, air from a nozzle 28a provided at the distal end of the distal hard portion 32 by an operation of closing a hole in a later-described air/water supply button 54b of the operation assembly 14, and discharges, for example, physiological saline from the nozzle 28a by a press operation of the air/water supply button 54b.

As shown in FIG. 1A, the insertion section 12 includes, from its distal end to proximal end, the distal hard portion 32, a bending portion 34, and a flexible tubular portion 36 in order. The proximal end of the insertion section 12, that is, the proximal end of the flexible tubular portion 36 is connected to the operation assembly 14.

Figure 2:
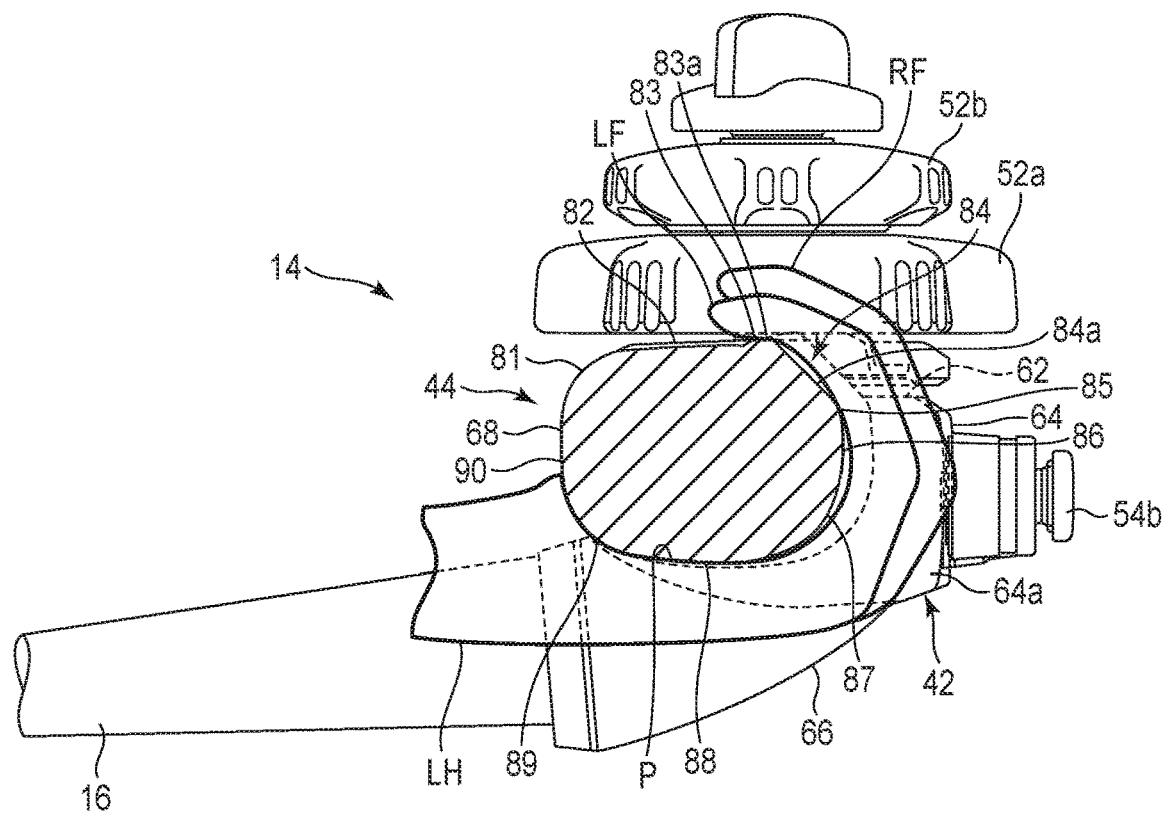
FIG. 2 is a schematic cross sectional view of an operation assembly of the endoscope according to the first embodiment along the line II-II in FIG. 1A.

As shown in FIG. 1A and FIG. 2, the operation assembly 14 includes an operation section 42 in which various mechanisms to be operated are provided, the grasp section (grip) 44 whose outer side is grasped by a user, and a protector 46 which prevents buckling of the insertion section 12. In the operation assembly 14, along its longitudinal axis L, the protector 46, the grasp section 44, and the operation section 42 are arranged in order from the side close to the insertion section 12 toward the side far from the insertion section 12. The proximal end of the flexible tubular portion 36 is connected to the protector 46 via an unshown mouth ring or the like.

On the outer peripheral surface of the operation section 42, bending operation knobs 52a and 52b, the suction button (fluid control button) 54a, the air/water supply button (fluid control button) 54b, and first to fourth switches 56a, 56b, 56c, and 56d are provided as some of the various mechanisms to be operated. The operation section 42 includes, as its outer peripheral surface and along a peripheral direction around the longitudinal axis L, a knob providing surface 62 in which the bending operation knobs 52a and 52b are provided, a button providing surface 64 in which the suction button 54a, the air/water supply button 54b, and the first and second switches 56a and 56b are provided, a support portion 66 in which the universal cord 16 extends and which is supported between the base of a thumb T and the base of an index finger IF of a left hand LH of the user, and a user facing surface (switch providing surface) 68 in which the fourth switch 56d is provided. The operation section 42 is provided, on an upper end of the operation section 42, with the third switch 56c. In addition, suitable functions are set to the first to fourth switches 56a, 56b, 56c, and 56d, respectively.

Furthermore, in a state where the user facing surface 68 is disposed face to face with the user, the support portion 66 is mounted on the index finger IF of the left hand LH of the user. At this point, in actuality, the support portion 66 is supported at a position from a part between the base of the thumb T and the base of the index finger IF of the left hand LH of the user to the back of the hand. Then the lower surface of the universal cord 16 is supported in the vicinity of the base of the thumb T. That is, the universal cord 16 is supported at the position from the part between the base of the thumb T and the base of the index finger IF of the hand of the user to the back of the hand. Further, the user disposes the thumb T of the left hand LH on the operation section 42 or the knobs 52a and 52b over the lower surface of the universal cord 16.

The knobs 52a and 52b can remotely operate the bending portion 34 of the insertion section 12. The bending portion 34 can be curved in a U-direction or a D-direction by the rotation of the bending operation knob 52a. The bending portion 34 can be curved in an R-direction or an L-direction by the rotation of the bending operation knob 52b. The rotation axis of the bending operation knobs 52a and 52b is substantially orthogonal to the longitudinal axis L.

A step 64a is formed between the knob providing surface 62, the button providing surface 64, and the support portion 66 of the operation section 42, and later-described second and third grip surfaces 82 and 84 of the grasp section 44.

The grasp section 44 is cylindrically shaped, and has the proximal opening 26a of the channel 26. The proximal opening 26a of the channel is disposed at a position close to the protector 46 in the grasp section 44 located between the operation section 42 and the protector 46.

FIG. 2 shows the outer casing shape of the grasp section 44 along the line II-II in FIG. 1A. That is, in FIG. 2, the operation assembly 14 is seen from the side of the grasp section 44 toward the side of the operation section 42. In addition, internal objects provided inside the grasp section 44 are not shown here; such as the illumination optical system 22, the observation optical system 24, the air/water supply path 28 that have been described above, and the mechanism used to curve the bending portion 34. The internal objects are not shown in FIG. 3 to FIG. 8 either.

Figure 3:
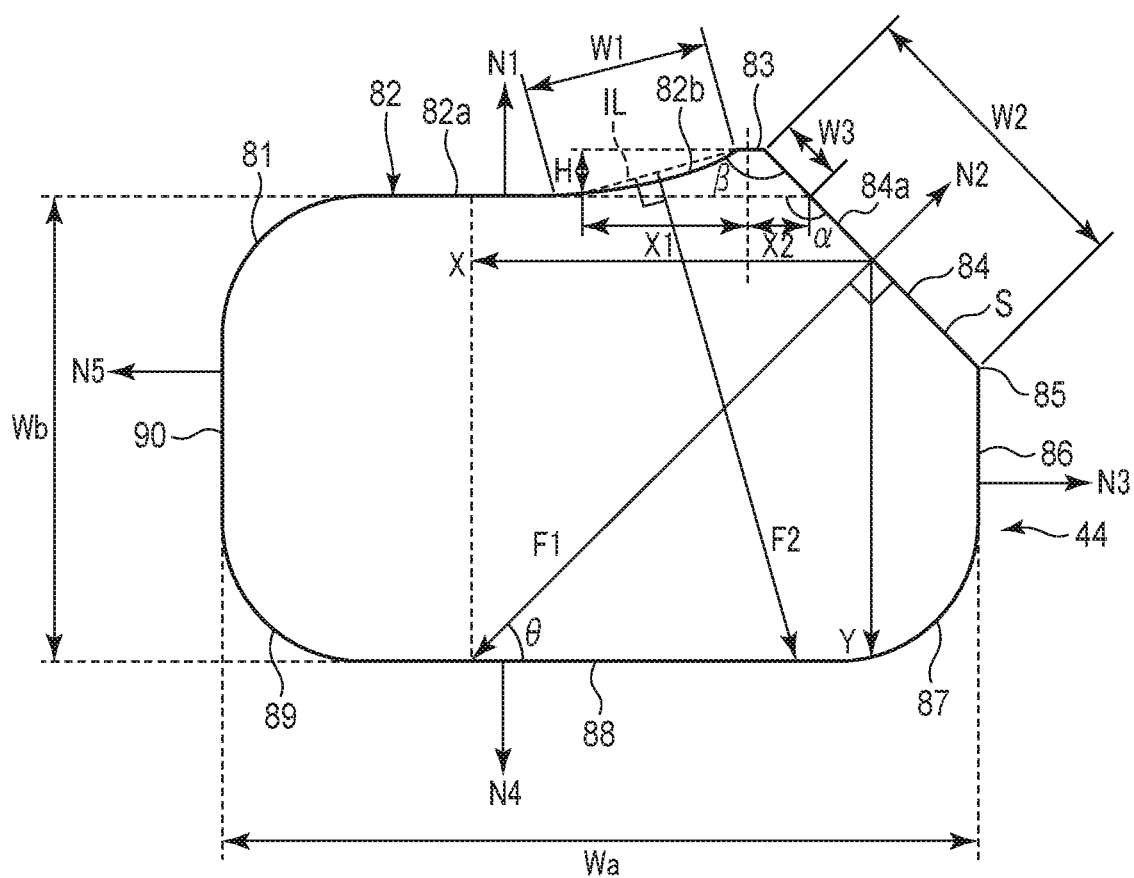
FIG. 3 is a schematic diagram showing a grasp section in FIG. 2, of the operation assembly of the endoscope according to the first embodiment.

FIG. 3 schematically shows the outer casing shape of the grasp section 44 shown in FIG. 2. As shown in FIG. 2 and FIG. 3, the grasp section 44 has, as its outer peripheral surface and in a peripheral direction around the longitudinal axis L, the first grip surface (knob side grip surface) 82, the second grip surface 84, a third grip surface (protruding portion side grip surface (button side grip surface)) 86, a fourth grip surface (palm disposing surface) 88, and a fifth grip surface (user facing surface) 90 which faces the user grasping the operation assembly 14. In the grasp section 44, the outer peripheral surface in the peripheral direction around the longitudinal axis L is annularly formed by the cooperation of the first to fifth grip surfaces 82, 84, 86, 88, and 90. Thus, the grasp section 44 is cylindrically shaped by the cooperation of the first to fifth grip surfaces 82, 84, 86, 88, and 90, and is grasped by the user. In addition, the grasp section 44 is provided between the insertion section 12 and the operation section 42 along the longitudinal axis L.

The third grip surface 86 is formed as a side surface disposed between the first grip surface 82 and the fourth grip surface 88. It is appropriate that a part (a later-described flat portion 82a) of the first grip surface 82 and the third grip surface 86 be disposed substantially at 900 to each other via the second grip surface 84. It is appropriate that the fourth grip surface 88 adjacent to the third grip surface 86 be disposed substantially at 90° to the third grip surface 86. It is appropriate that the fifth grip surface 90 adjacent to the fourth grip surface 88 be disposed substantially at 90° to the fourth grip surface 88. It is appropriate that the part (flat portion 82a) of the first grip surface 82 adjacent to the fifth grip surface 90 be disposed substantially at 90° to the fifth grip surface 90.

The first grip surface 82 is defined as a "first surface (base surface)", and the fourth grip surface 88 is defined as a "second surface". The fourth grip surface 88 defined as the "second surface" is formed on the back side of the first grip surface (first surface) 82 with respect to the longitudinal axis L. It is appropriate that the first grip surface 82 and the fourth grip surface 88 have portions parallel to each other. Thus, it is preferable that a normal line N1 to the first grip surface 82 and a normal line N4 to the fourth grip surface 88 are in directions substantially opposite to each other. It is appropriate that the third grip surface 86 and the fifth grip surface 90 have portions parallel to each other. Thus, it is preferable that a normal line N3 to the third grip surface 86 and a normal line N5 to the fifth grip surface 90 are in directions substantially opposite to each other. The second grip surface 84 has an inclined surface (a defining surface of later-described grasping force application direction F1) 84a which is inclined with respect to the first grip surface 82 and each of the third to fifth grip surfaces 86, 88, and 90. Thus, a normal line N2 to the second grip surface 84 is inclined with respect to each of the normal lines N1, N3, M4, and N5 to the first grip surface 82 and the third to fifth grip surfaces 86, 88, and 90.

As shown in FIG. 3, a Y-axis is taken parallel to the normal lines N1 and N4 in planar regions of the first grip surface 82 and the fourth grip surface 88, and an X-axis is taken parallel to the normal lines N3 and N5 in planar regions of the third grip surface 86 and the fifth grip surface 90. The width (length) of the fourth grip surface 88 in the X-axis direction is Wa, and the width (length) of the fifth grip surface 90 in the Y-axis direction is Wb. It is preferable that the width Wa is greater than the width Wb at positions of the grasp section 44 closer to the operation section 42 than the protector 46 shown in FIG. 1. In addition, the widths Wa and Wb may be substantially the same at positions of the grasp section 44 closer to the protector 46 shown in FIG. 1.

As shown in FIG. 2, the first grip surface 82 of the grasp section 44 is adjacent to the knob providing surface 62 of the operation section 42 along the longitudinal axis L. The second grip surface 84 of the grasp section 44 is adjacent to the knob providing surface 62 and the step 64a of the operation section 42 along the longitudinal axis L. The third grip surface 86 of the grasp section 44 is adjacent to the step 64a of the operation section 42 along the longitudinal axis L. The fourth grip surface 88 of the grasp section 44 is adjacent to the support portion 66 of the operation section 42 along the longitudinal axis L. The fifth grip surface 90 of the grasp section 44 is adjacent to the user facing surface 68 of the operation section 42 along the longitudinal axis L. It is preferable that the boundary between the user facing surface 68 of the operation section 42 and the fifth grip surface 90 of the grasp section 44 are formed continuously with each other without any step into, for example, a substantially flat shape.

Figure 4:
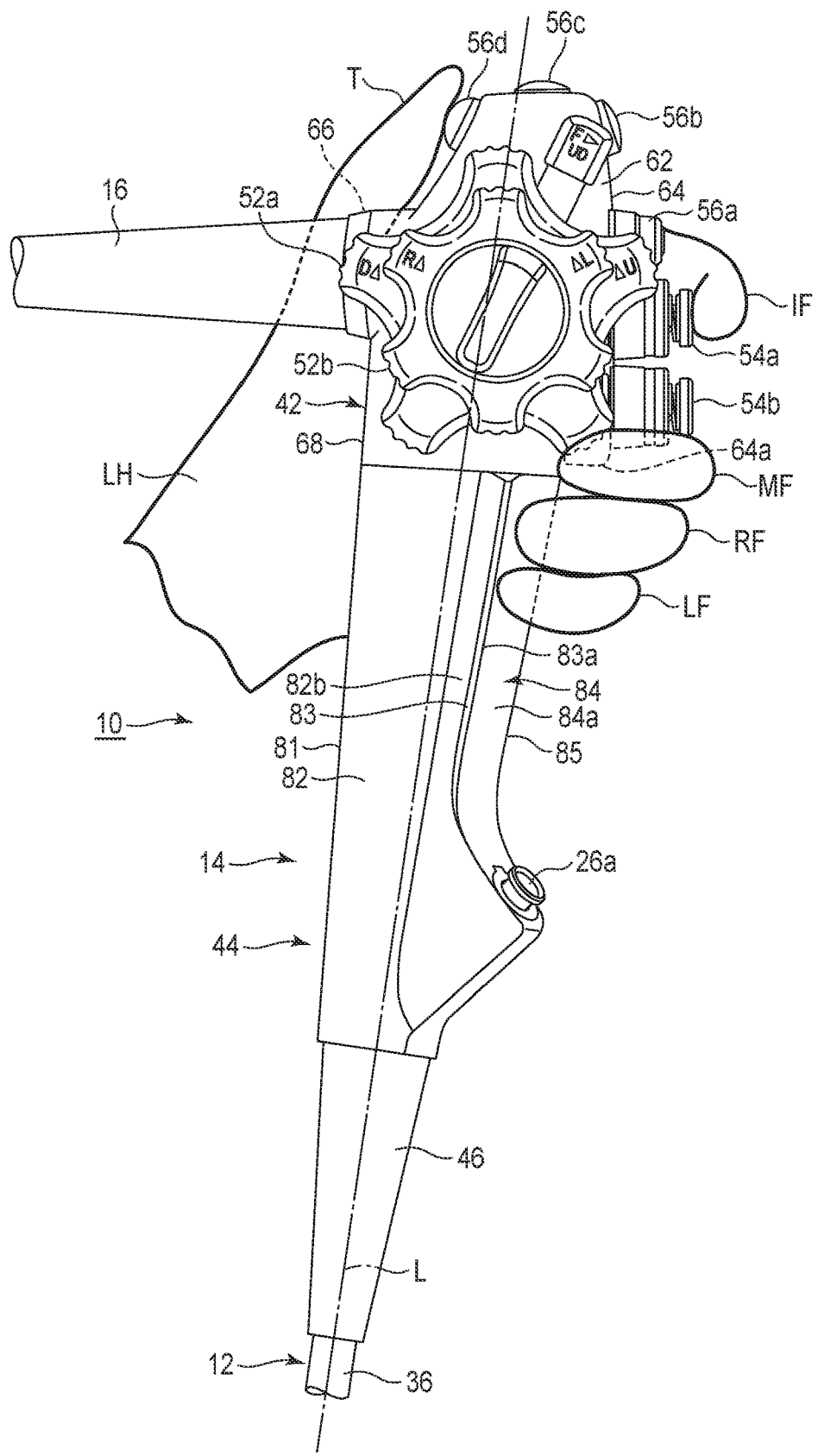
FIG. 4 is a schematic diagram showing a state where a user with relatively small hands grasps the operation assembly of the endoscope according to the first embodiment.

As shown in FIG. 2 and FIG. 3, a protruding portion 83 formed to protrude in a direction in which the knobs 52a and 52b are provided (an extending direction of the normal line N1 to the first grip surface 82) is provided in the first grip surface 82 at a position adjacent to the first grip surface 82 around the longitudinal axis L. As shown in FIG. 2 to FIG. 4, the protruding portion 83 radially outwardly protruding from the first grip surface 82 with respect to the longitudinal axis L forms a ridge (ridgeline) 83a which axially continuously forms a peak (crest) in a longitudinal direction L. The ridge 83a and the inclined surface 84a of the protruding portion 83 are adjacent to each other in the peripheral direction around the longitudinal axis L. It is preferable that the ridge 83a is formed as a curved surface with a suitable width of, for example, several millimeters along the peripheral direction around the longitudinal axis L. Particularly, it is preferable that a top having a radius R set to, for example, 1 mm to 5 mm is formed in the ridge 83a in the peripheral direction (width direction). The ridge 83a is formed from the upper end toward the lower end of the grasp section 44. The ridge 83a does not need to be formed from the upper end to the lower end of the grasp section 44, and has only to be formed, for example, in a part which a ring finger RF and/or a little finger LF touch.

The first grip surface 82 has the flat portion (first surface) 82a which is substantially a flat surface, and an inclined surface (first inclined surface) 82b formed between the flat portion 82a and the ridge 83a of the second grip surface 84. The flat portion 82a of the first grip surface 82 is not limited to the flat surface, and may be a curved surface, or may have suitable projections and depressions or a step formed therein. A height H of the ridge 83a of the second grip surface 84 from the flat portion 82a by the inclined surface 82b of the first grip surface 82 is formed to be smaller than the width Wb.

When the flat portion 82a of the first grip surface 82 imaginarily extends toward the inclined surface (flat portion) 84a of the second grip surface 84, an X-axis direction component X1 of the inclined surface 82b of the first grip surface 82 is greater than an X-axis direction component X2 from the ridge 83a to the inclined surface (slope) 84a of the second grip surface 84. Thus, the length of the inclined surface 82b of the first grip surface 82 is formed to be greater than a later-described width W3. That is, the area of the inclined surface 82b of the first grip surface 82 is increased. Therefore, the inclined surface 82b of the first grip surface 82 has as large a contact area as possible, for example, when the balls of the ring finger RF and/or the little finger LF of the left hand LH of the user with relatively large hands are put on the inclined surface 82b, so that the grasping force is easily exerted on the grasp section 44 by the entire balls of the ring finger RF and/or the little finger LF of the left hand LH.

It is preferable that the inclined surface 82b of the first grip surface 82 is formed as a curved surface. Accordingly, the inclined surface 82b of the first grip surface 82 can have a larger area than when formed as a flat surface, and is appropriate to mount the balls of the ring finger RF and/or the little finger LF of the left hand LH of the user. An imaginary line IL which imaginarily connects a boundary part between the flat portion 82a and the inclined surface 82b of the first grip surface 82 to the ridge 83a of the second grip surface 84 is defined. The virtual line IL defines a width W1 of the inclined surface 82b of the first grip surface 82. That is, the width between the boundary part between the flat portion 82a and the inclined surface 82b of the first grip surface 82, and the ridge 83a of the second grip surface 84 is W1. The width W1 is smaller than a later-described width W2. The inclined surface 82b of the first grip surface 82 is formed as a downwardly protruding curved surface with respect to the imaginary line IL. Thus, the flat portion 82a and the inclined surface 82b of the first grip surface 82 can be smoothly continuous without any step. In this instance, production of a possible space is prevented between the balls of the ring finger RF and/or the little finger LF of the left hand LH of the user, and the boundary between the flat portion 82a and the inclined surface 82b of the first grip surface 82.

In addition, if the inclined surface 82b is flat or upwardly protruding with respect to the imaginary line IL, a boundary (see FIG. 5B and FIG. 7B) is formed between the flat portion 82a and the inclined surface 82b of the first grip surface 82, depending on the size of the length X1. In this instance, a space can be easily produced between the balls of the ring finger RF and/or the little finger LF of the left hand LH of the user, and the boundary between the flat portion 82a and the inclined surface 82b of the first grip surface 82.

Moreover, the inclined surface 84a is provided, in the protruding portion 83, on the side opposite to the inclined surface 82b of the first grip surface 82 across the ridge 83a of the protruding portion 83, connects the ridge 83a and the third grip surface 86 to each other, and is inclined with respect to the first grip surface 82 (the flat portion 82a) and the third grip surface 86.

As shown in FIG. 2 and FIG. 3, an edge portion 85 is formed between the inclined surface (second inclined surface) 84a of the second grip surface 84 and the third grip surface (side surface) 86. That is, the edge portion 85 is formed at a position closer to the fourth grip surface (first surface) 88 than the second grip surface (first surface) 82. The edge portion 85 extends from the upper end toward the lower end of the grasp section 44, and defines the inclined surface 84a of the second grip surface 84 between the edge portion 85 and the ridge 83a. The edge portion 85 may be formed as a flat surface or a curved surface with a suitable width of, for example, several millimeters along the peripheral direction around the longitudinal axis L, in the same manner as the ridge 83a. The edge portion 85 is formed from the upper end toward the lower end of the grasp section 44. The edge portion 85 does not need to be formed from the upper end to the lower end of the grasp section 44.

The width (length) of the inclined surface 84a of the second grip surface 84 defined between the ridge 83a and the edge portion 85 is W2. Here, the ridge 83a having the height H is formed in the second grip surface 84 between the second grip surface 84 and the first grip surface 82. Thus, the width W2 of the inclined surface 84a of the second grip surface 84 can be greater by the width (length) W3 based on the height H than in a state where the ridge 83a is not formed by the inclined surface 82b of the first grip surface 82. Further, the volume of the internal space of the grasp section 44 can be maintained as much as possible by the presence of the ridge 83a. That is, the width W2 of the inclined surface 84a of the second grip surface 84 is increased by the width W3 to form the ridge 83a, and the decrease of the internal space of the grasp section 44 is thereby inhibited. It is therefore possible to secure a suitable volume when the unshown internal objects are disposed inside the grasp section 44.

In addition, the inclined surface 84a of the second grip surface 84 has the width W2 along the peripheral direction around the longitudinal axis L and is inclined with respect to the fourth grip surface 88 to the extent that the direction F1 in which later-described grasping force acting in a direction opposite to the normal line N2 is exerted by the balls of the ring finger RF and the little finger LF can be defined in a predetermined direction (a direction toward the fourth grip surface 88).

A curved surface 87 in which the bases of the fingers are disposed is formed between the third grip surface 86 and the fourth grip surface 88 by the cooperation of the third grip surface 86 and the fourth grip surface 88. A curved surface 89 in which a wrist-side part of a palm P is disposed is formed between the fourth grip surface 88 and the fifth grip surface 90 by the cooperation of the fourth grip surface 88 and the fifth grip surface 90. The part between the first grip surface 82 and the fifth grip surface 90, which the hand of the user does not touch at normal times, is preferably formed as a curved surface 81 by the cooperation of the first grip surface 82 and the fifth grip surface 90. It is appropriate that the curved surfaces 81, 87, and 89 be formed into shapes which radially outwardly protrude with respect to the longitudinal axis L.

The inclined surface 84a of the second grip surface 84 is used as an application direction defining surface of the grasping force to define the direction in which the grasping force to grasp with the ring finger RF and/or the little finger LF of the left hand LH of the user is exerted. It is preferable that the imaginary line (second imaginary line) F1 in a direction opposite to the normal line N2 originating from a central position of the inclined surface 84a of the second grip surface 84 along the peripheral direction (width direction) around the longitudinal axis L imaginarily crosses any position of the fourth grip surface 88 including the curved surfaces 87 and 89. That is, the virtual line F1 extends from the central position of the inclined surface (second inclined surface) 84a of the second grip surface 84 along the periphery of the longitudinal axis L. An angle θ between the fourth grip surface 88 and the imaginary line F1 in this instance is preferably, for example, about 45°. Thus, when the inclined surface 84a of the second grip surface 84 is grasped by the balls of the ring finger RF and/or the little finger LF of the left hand LH of the user, this grasping force is exerted toward the fourth grip surface 88. In addition, the direction of the imaginary line F1 opposite to the normal line N2 in the center of the width W2 of the second grip surface 84 has only to be brought toward the fourth grip surface 88 including the curved surfaces 87 and 89. Thus, the inclination angle of the inclined surface 84a of the second grip surface 84 with respect to the flat portion 82a of the first grip surface (first surface) 82 is suitably set within the range in which the imaginary line F1 crosses the fourth grip surface 88.

Moreover, when the inclined surface 84a of the second grip surface 84 is a flat surface, an angle α of the inclined surface 84a of the second grip surface 84 to the flat portion 82a of the first grip surface 82 is an obtuse angle. That is, the angle α of a surface S defined by the ridge 83a of the protruding portion 83 of the second grip surface 84 and the edge portion 85 to the flat portion 82a of the first grip surface 82 is an obtuse angle. On the other hand, it is appropriate that an angle β of the inclined surface 84a of the second grip surface 84 to the inclined surface 82b of the first grip surface 82 be an obtuse angle, but may be an acute angle depending on the position where the imaginary line F1 crosses the fourth grip surface 88.

Now, effects of the endoscope 10 according to this embodiment are described.

First, an example in which a user with relatively small hands grasps the operation assembly 14 of the endoscope 10 is described with reference to FIG. 4 and FIG. 5A.

The user mounts the support portion 66 on the index finger IF of the left hand LH of the user in a state where the user facing surface 68 of the operation section 42 and the fifth grip surface 90 of the grasp section 44 directly face the user. The user puts the thumb T of the left hand LH on the user facing surface 68 of the operation section 42 or the knobs 52a and 52b over the lower surface of the universal cord 16.

Most of the palm P of the left hand LH of the user is disposed on the fourth grip surface 88. The wrist-side of the palm P of the left hand LH of the user can also be disposed on the fifth grip surface 90 (see FIG. 2). The index finger IF is disposed in the vicinity of the buttons 54a and 54b or the first switch 56a. A middle finger MF is disposed at a position at which the middle finger MF can support the knob 52a over the button providing surface 64 or the lower surface of the step 64a.

In this way, when the user appropriately grasps the operation assembly 14 of the endoscope 10 with the left hand LH, the user facing surface 68 and the fifth grip surface 90 can face the front of the user. In a state where the user facing surface 68 and the fifth grip surface 90 face the front of the user, the bending operation knobs 52a and 52b are disposed on the right side of the user, and the universal cord 16 is disposed on the left side of the user.

Figure 5A:
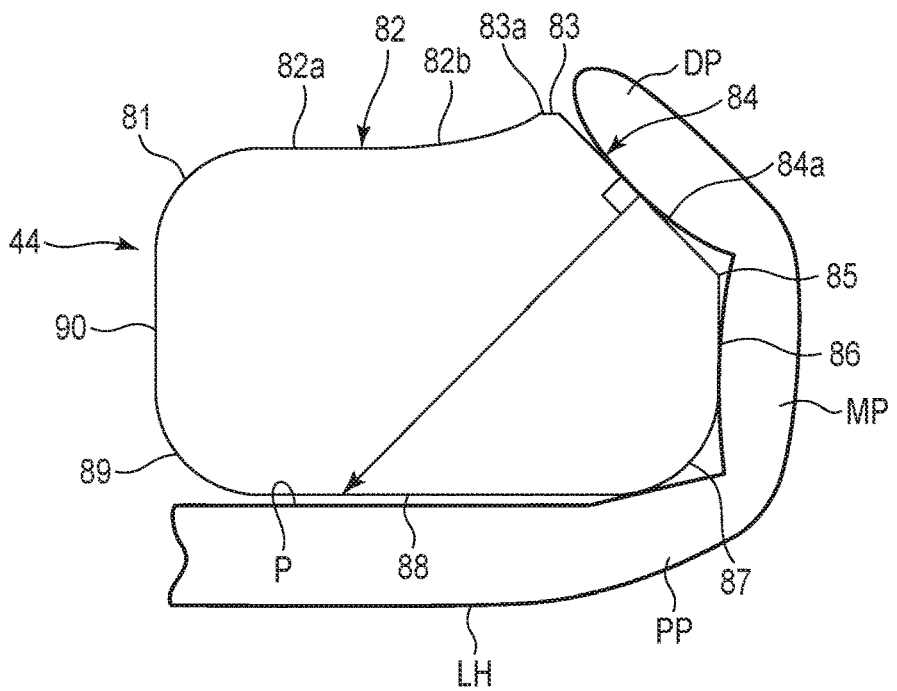
FIG. 5A is a schematic diagram showing a state where the user with relatively small hands grasps the grasp section of the operation assembly of the endoscope according to the first embodiment.

Then, as shown in FIG. 5A, the balls of the ring finger RF and the little finger LF are disposed on the second grip surface 84. At this point, for example, distal portions DP of the ring finger RF and the little finger LF are disposed on the second grip surface 84, middle portions MP are disposed on the third grip surface 86, and proximal portions PP are disposed on the fourth grip surface 88 including the curved surface 87.

The user with relatively small hands puts the entire balls of the ring finger RF and the little finger LF into surface contact with the inclined surface 84a of the second grip surface 84. Thus, the user with relatively small hands can have the surface contact of the fingers RF and LF with the inclined surface 84a of the second grip surface 84. Therefore, even the user with relatively small hands has the surface contact of the fingers RF and LF with the inclined surface 84a of the second grip surface 84, so that when appropriately grasping the operation assembly 14 of the endoscope 10 according to the present embodiment, the fingers RF and LF avoid slipping on the inclined surface 84a of the second grip surface 84 and the user easily maintains grasping force in a state where the user is grasping the operation assembly 14 for a long time. Further, the width W2 of the inclined surface (second inclined surface) 84a of the second grip surface 84 around the longitudinal axis L is greater than the width W1 of the inclined surface (first inclined surface) 82b of the first grip surface 82 around the longitudinal axis L. Moreover, the inclined surface 82b of the first grip surface 82 and the inclined surface 84a of the second grip surface 84 extend along the longitudinal axis L. Thus, if the widths W1 and W2 of the inclined surface 82b of the first grip surface 82 and the inclined surface 84a of the second grip surface 84 and their directions along the longitudinal axis L are taken into consideration, the area of contact of the fingers RF and LF in the inclined surface 84a of the second grip surface 84 is larger than the area of contact of the fingers RF and LF in the inclined surface 82b of the first grip surface 82. Therefore, even the user with relatively small hands can keep the fingers RF and LF in contact with the inclined surface 84a of the second grip surface 84 in a region of a larger area. Thus, when the user with relatively small hands grasps the operation assembly 14 of the endoscope 10 according to the present embodiment, the user can stably grasp the operation assembly 14. Moreover, even if the usage time of the endoscope 10 increases, the user can keep grasping while maintaining sufficient grasping force because surface pressure on the balls of the fingers RF and LF can be received by the entire balls of the fingers.

The grasping force is applied to the inclined surface 84a of the second grip surface 84 by the balls of the ring finger RF and the little finger LF. The direction F1 of the grasping force is not brought toward the fifth grip surface 90 but is brought toward the fourth grip surface 88 in which most of the palm P is disposed. That is, the grasp section 44 of the operation assembly 14 of the endoscope 10 according to this embodiment defines, on the fourth grip surface 88 supported by the palm P, the direction F1 of the grasping force applied to the inclined surface 84a of the second grip surface 84 in a state where the operation assembly 14 is grasped. Thus, even if the inclined surface 82b of the first grip surface 82 adjacent, along the longitudinal axis L, to the surface 62 in which the knobs 52a and 52b are provided can not be grasped, the grasping force on the inclined surface 84a of the second grip surface 84 by the balls of the ring finger RF and the little finger LF acts as force to press the fourth grip surface 88 to the palm P. In this way, stable grasping state is maintained by pressing the fourth grip surface 88 to the palm P. Therefore, when appropriately grasping the operation assembly 14 of the endoscope 10 according to the present embodiment, even the user with relatively small hands can keep a state in which sliding is difficult while the user keeps grasping the grasp section 44 for a long time, and the user easily maintains grasping force. In addition, by hooking the fingers on the edge portion 85, the user with relatively small hands can also keep a state in which sliding is difficult while the user keeps grasping the grasp section 44, and the user can easily maintain the grasping force.

Figure 5B:
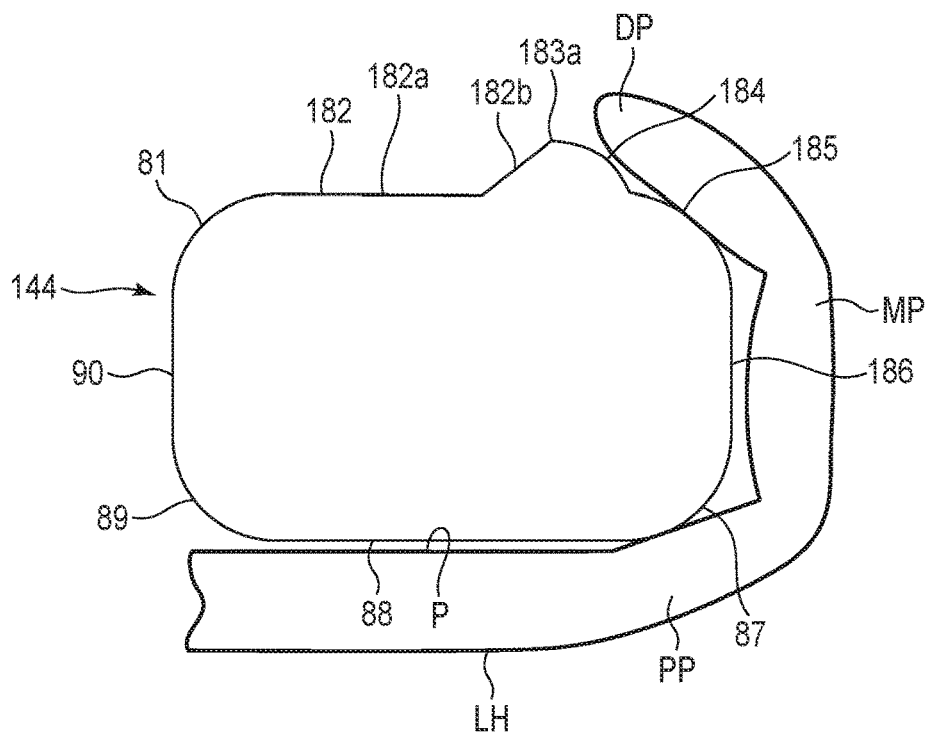
FIG. 5B is a schematic diagram showing a state where the user with relatively small hands grasps a grasp section as a reference example for comparison with the grasp section of the operation assembly of the endoscope according to the first embodiment.

Here, an example of a grasp section 144 in which the second grip surface 84 is not formed is shown in FIG. 5B as a reference for comparison with the grasp section 44 according to the present embodiment. For example, the distal portions DP of the ring finger RF and the little finger LF are disposed on a curved surface 185, the middle portions MP are disposed on a third grip surface 186, and the proximal portions PP are disposed on the fourth grip surface 88 including the curved surface 87. It is difficult for the user with relatively small hands to have the fingers RF and LF reach a first grip surface 182. Thus, a contact part between the fingers RF and LF of the user and the grasp section 144 is the curved surface 185. That is, in the example shown in FIG. 5B, the balls of the ring finger RF and the little finger LF touch the curved surface 185 between the first grip surface 182 and the third grip surface 186. The balls of the ring finger RF and the little finger LF partly abut on the curved surface 185. Each of the curved surfaces 184 and 185 has a top, so that in the case of the user with relatively small hands, the balls of the ring finger RF and the little finger LF partly contact the curved surface 185, but contact of the entire balls of the fingers is difficult. Thus, even when the user with relatively small hands appropriately grasps the operation assembly of the endoscope shown in FIG. 5B, the ring finger RF and the little finger more easily slide than in the state shown in FIG. 5A, and keeping sufficient grasping force to grasp the operation assembly is difficult. If sliding is caused as above, parts of the balls of the ring finger RF and the little finger LF can press, for example, a region over the curved surfaces 184 and the third grip surface 186 in FIG. 5B. In this case, the grasping force is applied toward the fifth grip surface 90 rather than the palm P which supports the fourth grip surface 88. Thus, the force to press the grasp section 144 to the palm P is weakened.

Furthermore, in the example shown in FIG. 5B, there can be a case where force can not be applied toward the fourth grip surface 88 which the palm P touches, depending on the angle at which the balls of the ring finger RF and the little finger LF touch an inclined surface 182b. Thus, there can be a case where the force by the balls of the ring finger RF and the little finger LF may not act as the force to press to the palm P. In this case, sliding is easier than in the state shown in FIG. 5A.

In addition, in the description here, the middle finger MF is disposed at the position where the middle finger MF can support the bending operation knob 52a. It should be understood that the middle finger MF may be disposed in the second grip surface 84 in the same manner as the ring finger RF and/or the little finger LF. That is, the grasp section 44 can be generally grasped with one or more of the second to fourth fingers or with the two third and fourth fingers.

Figure 6:
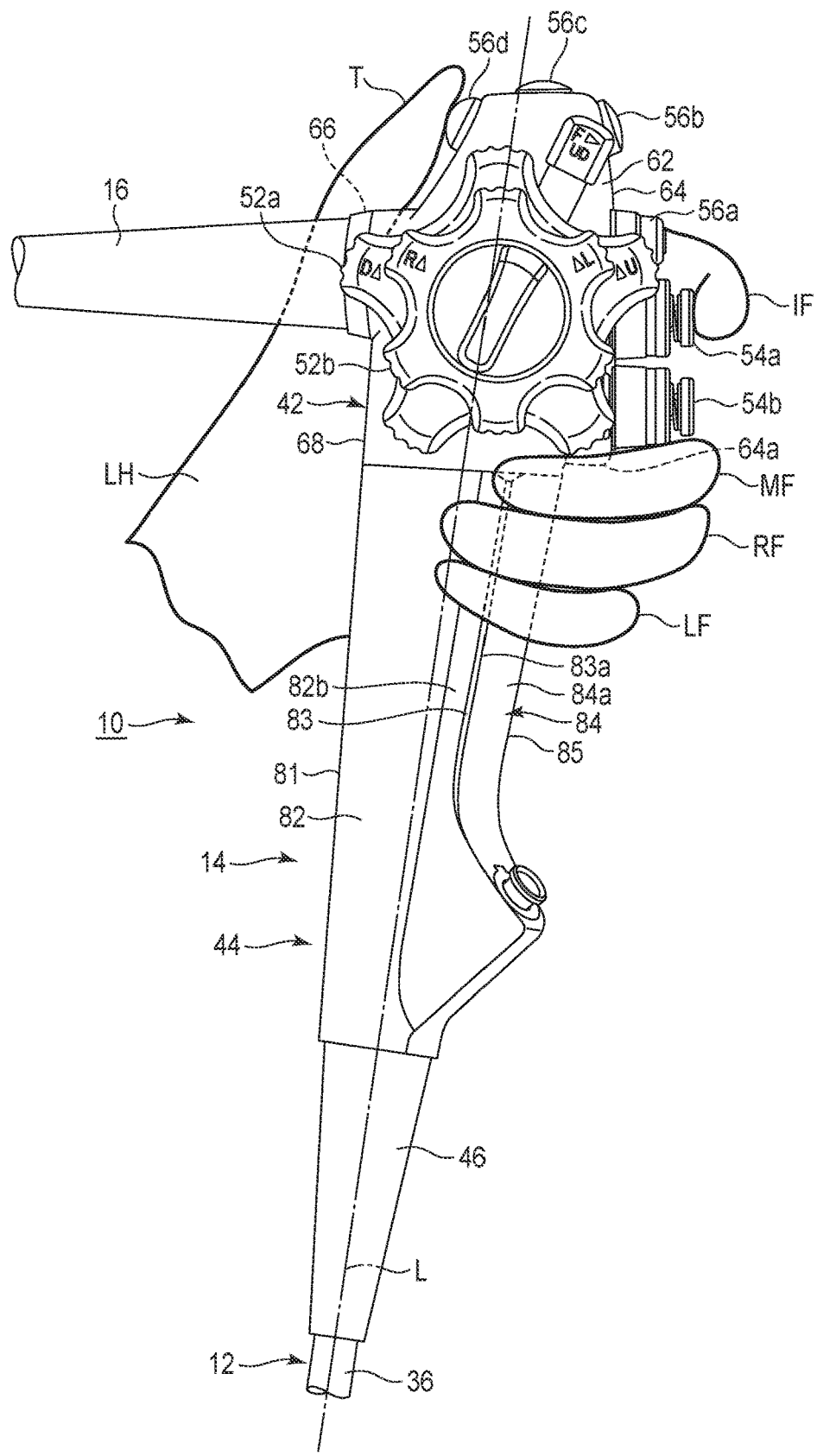
FIG. 6 is a schematic diagram showing a state where a user with relatively large hands grasps the operation assembly of the endoscope according to the first embodiment.
Figure 7A:
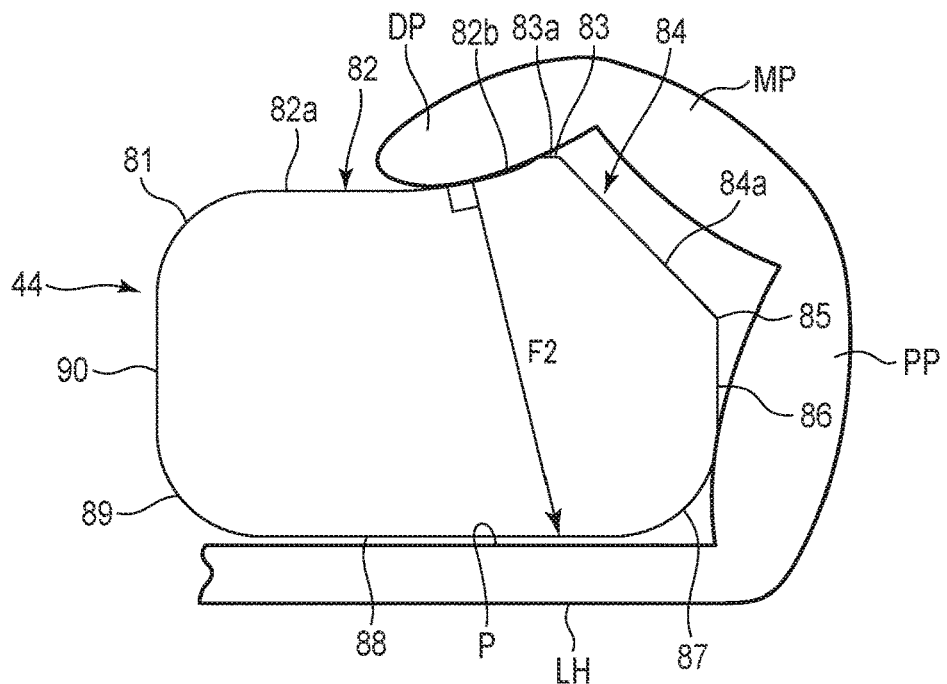
FIG. 7A is a schematic diagram showing a state where the user with relatively large hands grasps the grasp section of the operation assembly of the endoscope according to the first embodiment.

Now, an example in which the user with relatively large hands grasps the operation assembly 14 of the endoscope 10 is described with reference to FIG. 6 and FIG. 7A.

In the same manner as above, the user grasps the operation assembly 14 of the endoscope 10. Then, as shown in FIG. 7A, the balls of the ring finger RF and the little finger LF are disposed on the first grip surface 82. At this point, for example, the distal portions DP of the ring finger RF and the little finger LF are disposed on the inclined surface 82b of the first grip surface 82, the middle portions MP are disposed on the second grip surface 84, and the proximal portions PP are disposed on the third grip surface 86.

The user with relatively large hands puts the entire balls of the ring finger RF and the little finger LF into surface contact with the inclined surface 82b of the first grip surface 82. Thus, the user with relatively large hands can have the surface contact of the fingers RF and LF with the inclined surface 82b of the first grip surface 82. Therefore, even the user with relatively large hands has the surface contact of the fingers RF and LF with the inclined surface 82b of the first grip surface 82, so that when appropriately grasping the operation assembly 14 of the endoscope 10 according to the present embodiment, the fingers RF and LF avoid slipping on the inclined surface 82b of the first grip surface 82 and the user easily maintains grasping force in a state where the user is grasping the operation assembly 14 for a long time. Particularly, since the inclined surface 82b of the first grip surface 82 is a curved surface, the area of contact with the balls of the ring finger RF and the little finger LF is greater, and slide preventing effects are increased. Moreover, even if the usage time of the endoscope 10 increases, the user can keep grasping while maintaining sufficient grasping force because surface pressure on the balls of the fingers RF and/or LF can be received by the entire balls of the fingers.

Furthermore, the ridge 83a has a curved surface whose radius R is set to, for example, 1 mm to 5 mm. Thus, the area of contact between the ridge 83a and the fingers RF and LF is larger, and slide preventing effects are increased.

The grasping force is applied to the inclined surface 82b of the first grip surface 82 by the balls of the ring finger RF and the little finger LF. It is preferable that in the imaginary line IL, an imaginary line (first imaginary line) F2 which extends from the central position of the imaginary line IL in a direction orthogonal to the imaginary line IL crosses the inclined surface 82b of the first grip surface 82, and also imaginarily crosses any position of the fourth grip surface 88 including the curved surface 87. The direction F2 of the grasping force is brought toward the fourth grip surface 88 in which most of the palm P is disposed. That is, the grasp section 44 of the operation assembly 14 of the endoscope 10 according to this embodiment defines, on the fourth grip surface 88 supported by the palm P, the direction F2 of the grasping force applied to the inclined surface 82b of the first grip surface 82 in a state where the operation assembly 14 is grasped. Thus, the grasping force on the inclined surface 82b of the first grip surface 82 by the balls of the ring finger RF and the little finger LF acts as force to press the fourth grip surface 88 to the palm P. In this way, stable grasping state is maintained by pressing the fourth grip surface 88 to the palm P. Therefore, when appropriately grasping the operation assembly 14 of the endoscope 10 according to the present embodiment, even the user with relatively large hands can keep a state in which sliding is difficult while the user keeps grasping the grasp section 44 for a long time, and the user easily maintains grasping force. In addition, by hooking the fingers on the edge portion 85, the user with relatively large hands can also keep a state in which sliding is difficult while the user keeps grasping the grasp section 44, and the user can easily maintain the grasping force.

Figure 7B:
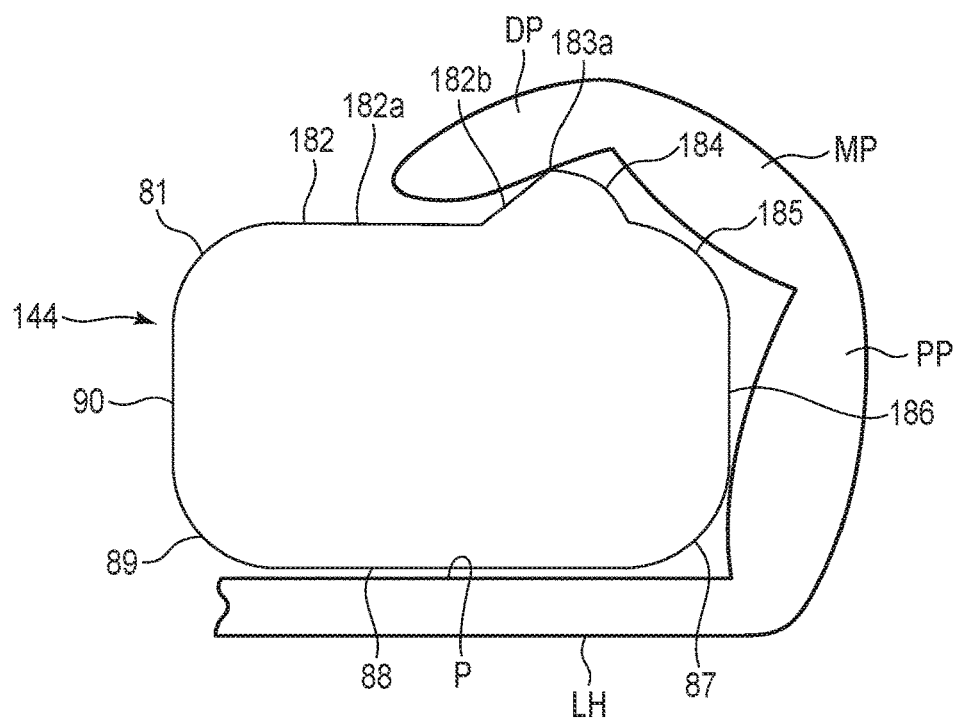
FIG. 7B is a schematic diagram showing a state where the user with relatively large hands grasps the grasp section as the reference example for comparison with the grasp section of the operation assembly of the endoscope according to the first embodiment.

Here, an example of the grasp section 144 in which the second grip surface 84 is not formed is shown in FIG. 7B as a reference for comparison with the grasp section 44 according to the present embodiment. For example, the distal portions DP of the ring finger RF and the little finger LF are disposed on the inclined surface 182b of the first grip surface 182 and a ridge 183a, the middle portions MP are disposed on the curved surface 185, and the proximal portions PP are disposed on the third grip surface 186. That is, in the example shown in FIG. 7B, the balls of the ring finger RF and the little finger LF touch a flat portion 182a of the first grip surface 182 and the inclined surface 182b by the ridge 183a. The inclined surface 182b is more inclined than the inclined surface 82b of the first grip surface 82 shown in FIG. 7A. In this instance, in the case of the user with relatively large hands, the balls of the ring finger RF and the little finger LF partly contact the inclined surface 182b. Thus, even when the user with relatively large hands appropriately grasps the operation assembly of the endoscope shown in FIG. 7B, it is more difficult for the user to keep the grasping force with the ring finger RF and the little finger LF than in the state shown in FIG. 7A, and it is easy for the ring finger RF and the little finger LF to slip.

In addition, in the description here, the middle finger MF is disposed at the position where the middle finger MF can press the bending operation knob 52a. It should be understood that the middle finger MF may be disposed in the inclined surface 82b of the first grip surface 82 in the same manner as the ring finger RF and/or the little finger LF.

The user firmly grasps the insertion section 12 with the unshown right hand in a state where the user grasps the operation assembly 14 of the endoscope 10 with the left hand LH as above.

Then the user suitably moves the right hand to perform an operation of twisting the insertion section 12. In this case, because the operation assembly 14 is fixed to the proximal portion of the insertion section 12, force to counteract the twisting of the insertion section 12 acts on the operation assembly 14. In this instance, even when the user with relatively small left hand or the user with relatively large left hand naturally grasps the operation assembly 14, the grasping force application directions F1 and F2 by the balls of the ring finger RF and the little finger LF are brought toward the fourth grip surface 88. Thus, a state where the fourth grip surface 88 is pressed to the palm P is maintained. This is also maintained when the operation assembly 14 grasped with the left hand LH is suitably moved in accordance with the motion of the insertion section 12 grasped with the right hand. Therefore, even if the force to counteract the twisting of the insertion section 12 is exerted, it is difficult for the balls of the ring finger RF and the little finger LF to slide on the grasp section 44, and it is easy to maintain a state where the operation assembly 14 is grasped. In this instance, sliding of the balls of the ring finger RF and the little finger LF is more difficult in the operation assembly 14 of the endoscope 10 according to this embodiment than in the operation assembly of the endoscope shown for reference in FIG. 5B and FIG. 7B.

As described above, the following can be said according to the endoscope 10 in this embodiment.

In the endoscope 10 according to this embodiment, the surface of the grasp section 44 adjacent, along the longitudinal axis L, to the surface (knob providing surface) 62 of the operation section 42 in which the bending operation knobs 52a and 52b are disposed is the first surface (first grip surface) 82, and then the ridge 83a which outwardly protrudes at the position adjacent to the first grip surface 82 in the peripheral direction around the longitudinal axis L is formed, and moreover, the inclined surface (defining surface) 84a is formed. The inclined surface (defining surface) 84a is provided on the side of the grasp section 44 opposite to the first surface along the peripheral direction around the longitudinal axis L as compared to the ridge 83a, and defines the application direction F1 of the grasping force of the grasp section 44 toward the fourth grip surface 88 on the side opposite to the first grip surface 82 when the user have a grasp. For example, when the user with relatively small hands disposes the ring finger RF, the little finger LF, and in some cases, the middle finger MF in the inclined surface 84a to grasp the grasp section 44, the user can apply the grasping force to the side opposite to the normal line N2 to the inclined surface 84a of the second grip surface 84. Thus, the fourth grip surface 88 can be pressed to the palm P by the grasping force originating from the ring finger RF and the little finger LF. Therefore, even the user with relatively small hands can secure the area of contact of the ring finger RF and the little finger LF with the grasp section 44, and the grasp section 44 of the operation assembly 14 can be stably grasped. Moreover, even the user with relatively large hands can grasp the part of the first grip surface (first surface) 82 adjacent to the ridge 83a with the balls of, for example, the ring finger RF and the little finger LF. Thus, when the user with relatively large hands holds the operation assembly 14, the fourth grip surface 88 can be pressed to the palm P by the grasping force originating from the ring finger RF and the little finger LF. Therefore, even the user with relatively large hands can secure the area of contact of the ring finger RF and the little finger LF with the grasp section 44, and the grasp section 44 of the operation assembly 14 can be stably grasped.

As above, according to the endoscope 10 in this embodiment, the first grip surface 82 or the second grip surface 84 is suitably grasped with one or more of the first to fourth fingers or with the third and fourth fingers, and the direction in which the grasping force is applied is defined, so that sliding on the grasp section 44 is difficult, and stable grasping is possible.

Particularly, the imaginary line F1 in a direction opposite to the normal line N2 to the inclined surface 84a of the second grip surface 84 crosses the fourth grip surface 88, so that even when the user with relatively small hands disposes the ring finger RF and the little finger LF in the inclined surface 84a, the grasping force can be certainly applied toward the fourth grip surface 88.

The inclined surface 84a of the second grip surface 84 is continuously formed adjacent to the ridge 83a, so that a relatively great width (breadth) W2 of the inclined surface 84a of the second grip surface 84 can be secured. Thus, when the width W2 of the inclined surface 84a is greater, the internal space of the grasp section 44 can be larger.

Because the ridge 83a is continuously formed in the first grip surface (first surface) 82, the area of contact by the balls of the ring finger RF and the little finger LF of the left hand LH of the user with relatively large hands can be secured.

The ridge 83a is provided on an edge of the second grip surface 84 in the peripheral direction around the longitudinal axis L, and the user with relatively large hands can hook the ring finger RF and/or the little finger LF on this ridge 83a for slide prevention use.

The proximal opening 26a of the treatment instrument insertion channel 26 is formed at a position of the second grip surface 84 close to the insertion section 12 (a position close to the protector 46). Because the second grip surface (inclined surface) 84 is formed up to the vicinity of the proximal opening 26a, the position of the grasp section 44 grasped by the user can be large, and a position to grasp can be freely decided.

Here, the ring finger RF and the little finger LF, or the middle finger MF is disposed in the inclined surface 82b of the first grip surface 82 of the grasp section 44 or the inclined surface 84a of the second grip surface 84. It is also appropriate that at least one of the ring finger RF, the little finger LF, and the middle finger MF be disposed in the inclined surface 82b of the first grip surface 82 of the grasp section 44 or the inclined surface 84a of the second grip surface 84 so that a suitable treatment by the endoscope 10 is carried out.

The inclined surface 84a of the second grip surface 84 may be formed as a protruding surface which radially outwardly protrudes with respect to the longitudinal axis L, preferably to the extent that this surface can be regarded as the same as a flat surface. The protruding shape of the inclined surface 84a of the second grip surface 84 is set in accordance with the contact area because grasping is more difficult if the area of contact with the balls of the ring finger RF and/or the little finger LF is smaller.

In the inclined surface 84a of the second grip surface 84, objects that provide slide preventing effects for the balls of the ring finger RF and/or the little finger LF may be formed; such as protruding portions, or a combination of protruding portions and depressed portions. The protruding portions, or the combination of the protruding portions and the depressed portions permit the tactual recognition of the position which the balls of the ring finger RF and/or the little finger LF touch. In this case, it is also appropriate that base portions of the protruding portions or the combination of the protruding portions and the depressed portions in the inclined surface 84a be formed as flat surfaces. That is, it is appropriate that at least a part of the inclined surface 84a has a flat surface shape. Moreover, when the combination of the protruding portions and the depressed portions is formed, at least some part of the inclined surface 84a can be said to be in a protruding shape, and at least some part of the inclined surface 84a can be said to be in a depressed shape.

The second embodiment is described with reference to FIG. 8. This embodiment is a modification of the first embodiment, and the same reference numbers are given as much as possible to the same members as the members described in the first embodiment, or the members having the same functions, and detailed descriptions are omitted.

Figure 8:
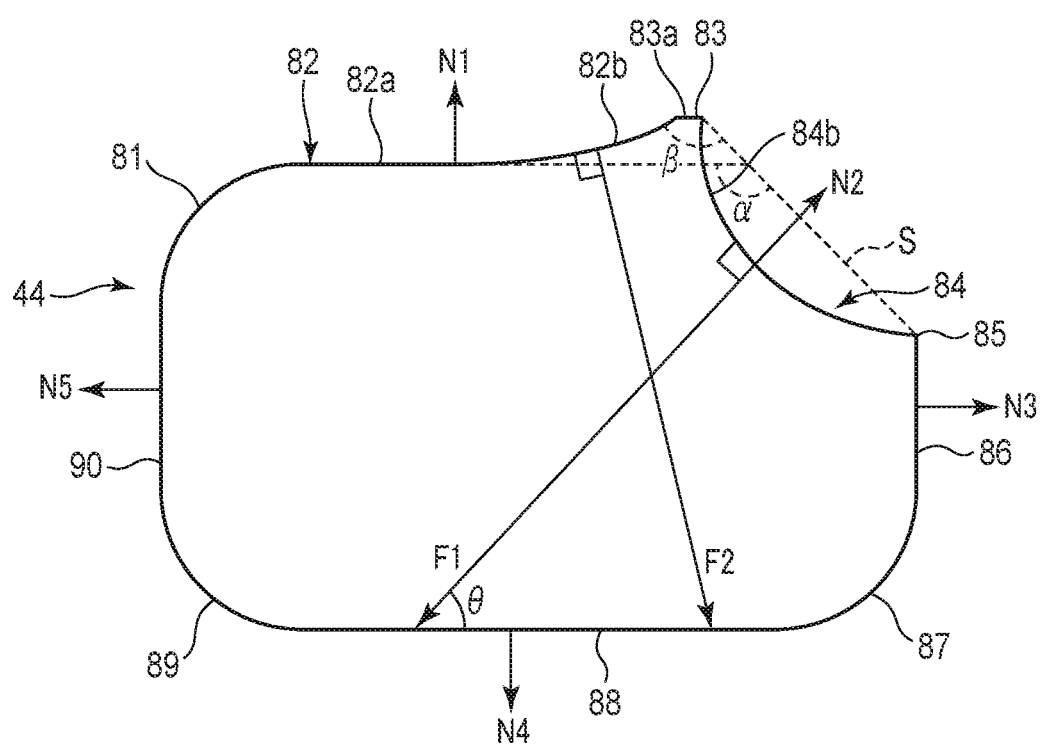
FIG. 8 is a schematic diagram showing the grasp section in FIG. 2, of the operation assembly of the endoscope according to the second embodiment.

As shown in FIG. 8, in this embodiment, an inclined surface 84b of the second grip surface 84 is formed into a depressed shape. That is, the inclined surface 84b is shaped to protrude toward the longitudinal axis L from an imaginary surface S defined by the ridge 83a and the edge portion 85. It is appropriate that this depressed inclined surface 84b be continuously formed with a suitable length from the upper end to the lower end of the grasp section 44. It is appropriate that the depth of the depressed inclined surface 84b be made, for example, to the extent that is smaller than the general thickness of the ring finger RF or the little finger LF of the user. When the inclined surface 84b has such a depth, the balls of the ring finger RF and/or the little finger LF easily abut on the bottom surface of the inclined surface 84b.

In the same manner as described in the first embodiment, the direction F2 in which the grasping force is applied by grasping with the balls of the ring finger RF and/or the little finger LF can be brought toward the fourth grip surface 88.

The surface (here, the imaginary surface) S defined by the ridge 83a of the second grip surface 84 and the edge portion 85 is located at a position of the obtuse angle α to the flat portion 82a of the first grip surface 82. On the other hand, it is appropriate that the virtual surface S of the second grip surface 84 be located at a position of the obtuse angle 3 to the inclined surface 82b of the first grip surface 82, but may be at a position of the acute angle depending on the position where the application direction F2 crosses the fourth grip surface 88.

Now, a first reference embodiment is described with reference to FIG. 9A and FIG. 9B. In this reference embodiment, the same reference numbers are given as much as possible to the same members as the members described in the first and second embodiments, or the members having the same functions, and detailed descriptions are omitted. Further, the structures of the suction button 54a and the air/water supply button 54b and the location of the universal cord 16 in this reference embodiment which will be described later can be suitably used in the operation assembly 14 of the endoscope 10 described in the first and second embodiments.

Figure 9A:
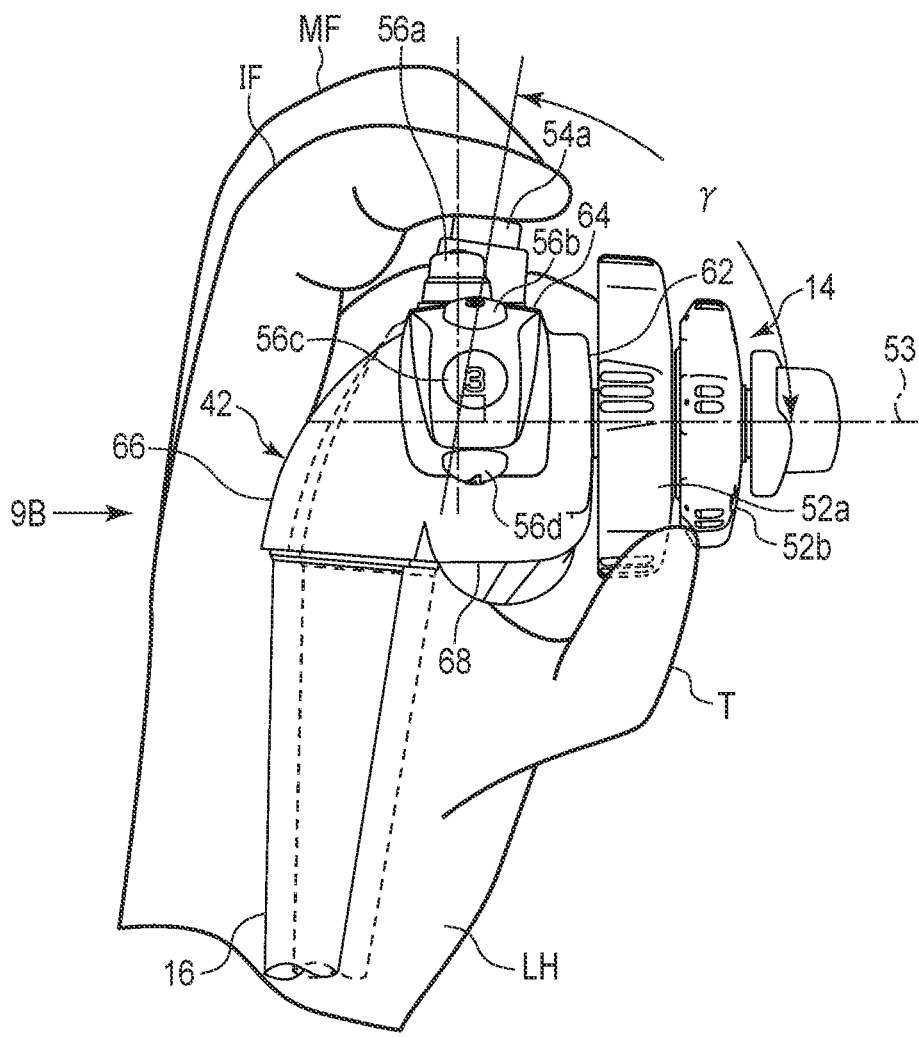
FIG. 9A is a schematic top view showing a state where the user grasps an operation assembly of an endoscope according to a first reference embodiment with the left hand.
Figure 9B:
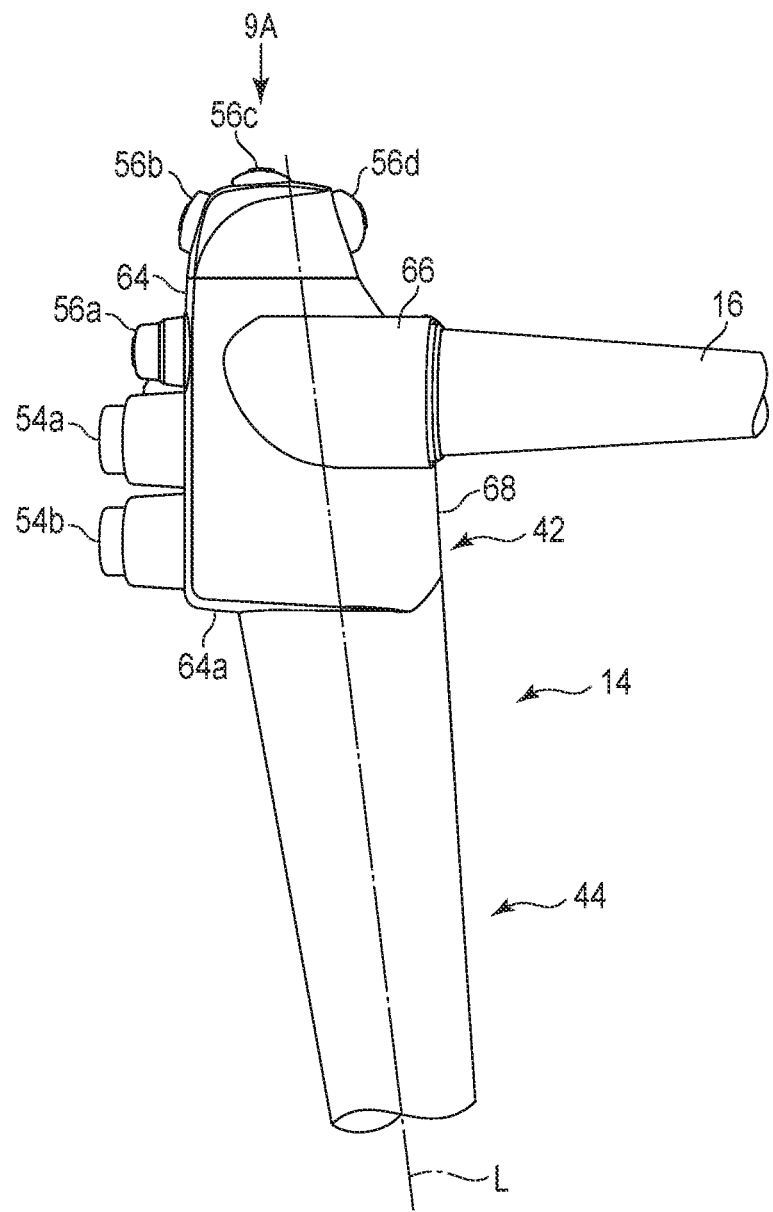
FIG. 9B is a schematic diagram showing a state where the operation assembly of the endoscope according to the first reference embodiment is seen from the opposite side of a knob disposing surface.

As shown in FIG. 9A, the press direction of the suction button 54a is formed at an angle γ (0°<γ<90°) to a rotation axis 53 of the bending operation knobs 52a and 52b. The press direction of the air/water supply button 54b is also formed at the angle γ (0°<γ<90°) to the rotation axis 53 of the bending operation knobs 52a and 52b. That is, the press directions of the buttons 54a and 54b are located obliquely toward the bending operation knobs 52a and 52b. In addition, here, as shown in FIG. 9B, the protruding heights of the buttons 54a and 54b from the button providing surface 64 are substantially the same. FIG. 9A is a view from a direction indicated by a reference mark 9A in FIG. 9B, so that the air/water supply button 54b is hidden behind the suction button 54a in FIG. 9A.

As shown in FIG. 9A, the universal cord 16 is formed so that its width along the axial direction of the rotation axis of the bending operation knobs 52a and 52b of the operation assembly 14 is greater than in a conventional state indicated by broken lines. Thus, the base of the thumb T of the left hand LH can be disposed on a far side, and, for example, the index finger IF and/or the middle finger MF more easily reach the switches 56a to 56d, the buttons 54a and 54b, and others.

When, for example, the index finger IF and/or the middle finger MF more easily reach the buttons 54a and 54b, the distance between the buttons 54a and 54b and the base sides of the index finger IF and/or the middle finger MF can be smaller. In this case, the index finger IF and/or the middle finger MF need to be greatly bent, but the bending amounts of the index finger IF and/or the middle finger MF can be reduced because the press directions of the buttons 54a and 54b are located obliquely toward the bending operation knobs 52a and 52b.

Therefore, the universal cord 16 is disposed more on the left side in FIG. 9A than before (see the broken lines in FIG. 9A), and the base of the thumb T is thus disposed on the far side so that the fingers more easily reach various switches and/or buttons, and at the same time, the buttons 54a and 54b are inclined to the side of the knobs 52a and 52b, whereby the buttons 54a and 54b are more easily operated even when the base sides of the fingers are close to the buttons 54a and 54b.

In FIG. 9A, according to this reference embodiment, the main press direction of the first switch 56a is defined in a direction orthogonal to the rotation axis 53. However, it is preferable to use the first switch 56a that can be operated by pressing not only from the direction orthogonal to the rotation axis 53 but also from various directions such as a sideward direction.

Now, a second reference embodiment is described with reference to FIG. 10A and FIG. 10B. In this reference embodiment, the same reference numbers are given as much as possible to the same members as the members described in the first and second embodiments, or the members having the same functions, and detailed descriptions are omitted. Moreover, the later-described location of the air/water supply button 54b in this reference embodiment can be suitably used in the operation assembly 14 of the endoscope 10 described in the first and second embodiments.

Figure 10A:
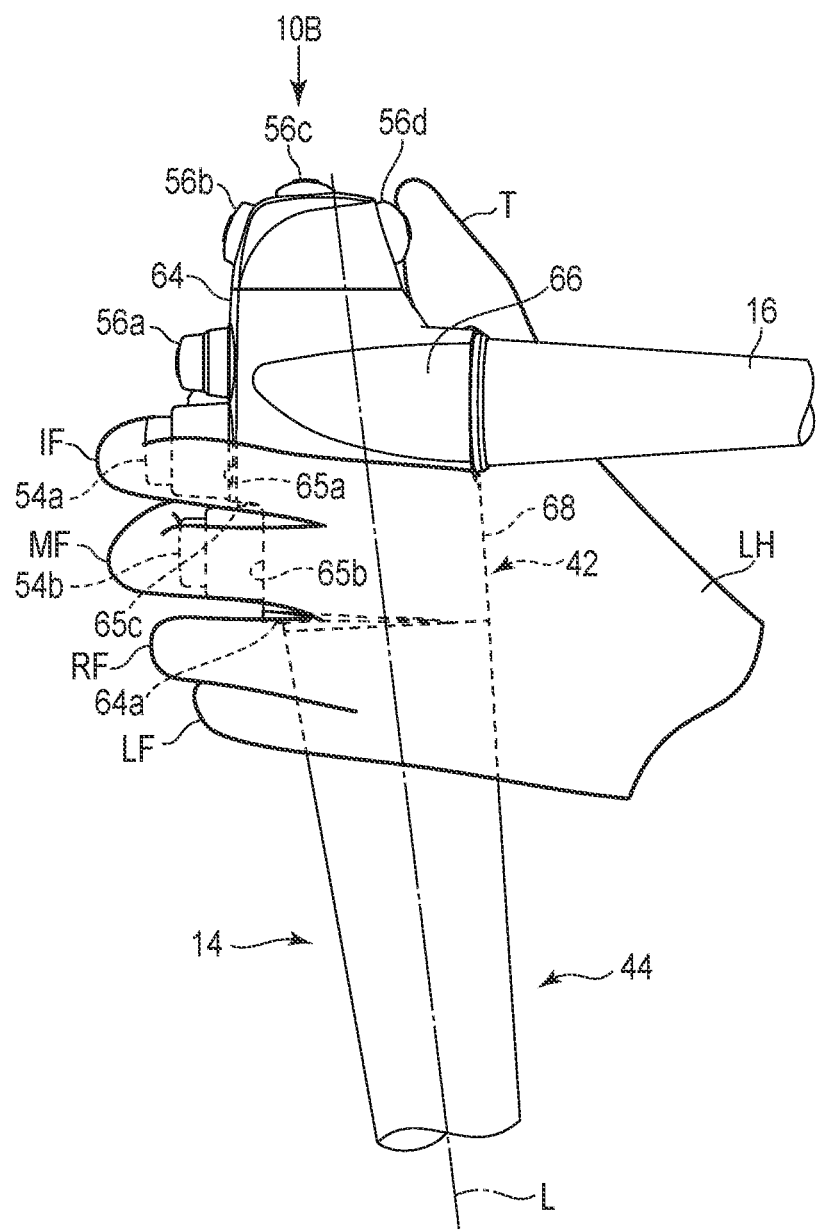
FIG. 10A is a schematic diagram showing a state where the user grasps an operation assembly of an endoscope according to a second reference embodiment with the left hand, which is seen from the opposite side of the knob disposing surface.

As shown in FIG. 10A, the button providing surface 64 has, by a step 65c, a distal surface (first mounting surface) 65a which is distal to the imaginary longitudinal axis L, and a proximal surface (second mounting surface) 65b which is proximal. The step 64a between the proximal surface 65b and the grasp section 44 is smaller than in a state shown in FIG. 1A and FIG. 2.

The suction button 54a is provided in the distal surface 65a. The air/water supply button 54b is provided in the proximal surface 65b. A press surface of the air/water supply button 54b is set to be closer to the virtual longitudinal axis L than a press surface of the suction button 54a. Thus, in FIG. 10B, the air/water supply button 54b is hidden behind the suction button 54a.

An assist operation of holding the bending operation knobs 52a and 52b may be performed by use of, for example, the middle finger MF. The location of the air/water supply button 54b as in this reference embodiment suppresses interference with the air/water supply button 54b caused when the bending operation knobs 52a and 52b are held with the middle finger MF and the ring finger RF. Thus, the assist operation of holding the bending operation knobs 52a and 52b is more easily performed.

Figure 10B:
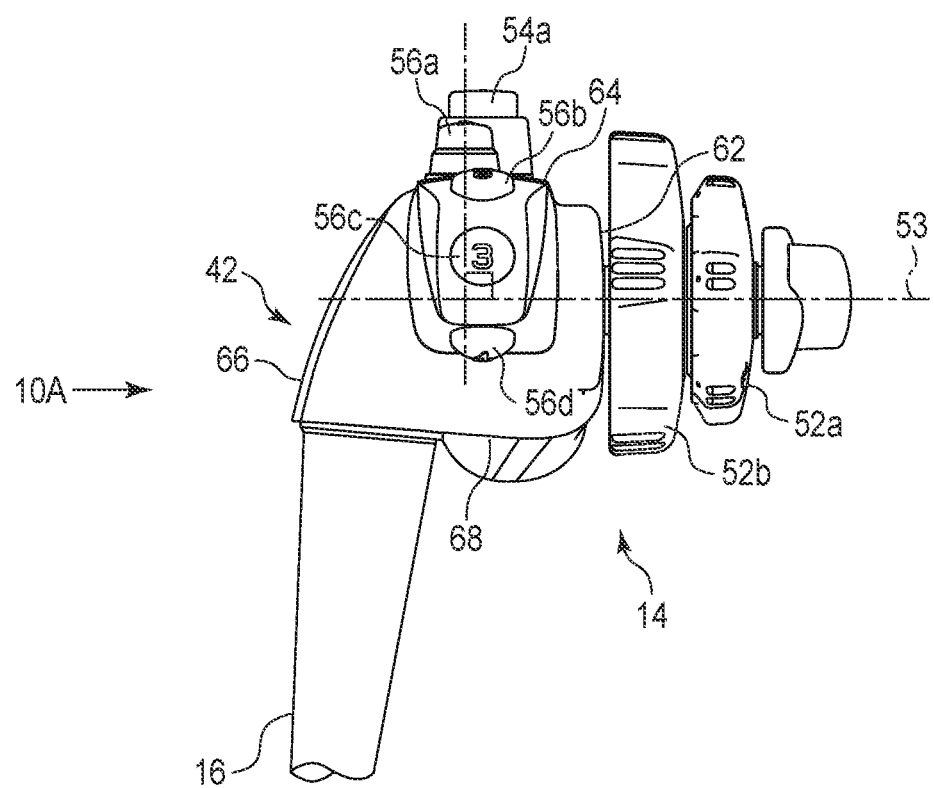
FIG. 10B is a schematic top view showing the operation assembly of the endoscope according to the second reference embodiment.

In addition, as shown in FIG. 10B, it is preferable here that press directions of the first switch 56a and the suction button 54a are orthogonal to the rotation axis 53 of the knobs 52a and 52b.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
    an insertion section that is configured to be inserted into a subject, the insertion section including a bendable bending portion and defining a longitudinal axis;
    an operation section that includes a bending operation knob that is configured to operate the bending portion, the bending operation knob being disposed on a knob providing surface;
    a grasp section that is disposed between the insertion section and the operation section and that is configured to be grasped by a user, the grasp section including:
        a first surface that is adjacent to the knob providing surface,
        a second surface that is disposed on an opposite side of the grasp section from the first surface with respect to the longitudinal axis, wherein the second surface includes a flat portion
        a side surface that is disposed between the first surface and the second surface,
        a protruding portion that forms a ridge that protrudes radially outwardly with respect to the first surface,
        a first inclined surface, with respect to a cross-section along an axis perpendicular to the longitudinal axis, that is disposed on the protruding portion at a side adjacent to the first surface and that is inclined with respect to the first surface, and
        a second inclined surface, with respect to a cross-section along an axis perpendicular to the longitudinal axis, that is disposed on the protruding portion at a side opposite to the first inclined surface across the ridge, the second inclined surface connecting the ridge and the side surface to each other and being inclined with respect to the first surface and the side surface, wherein one of the first inclined surface or the second inclined surface is not flat.

2. The endoscope according to claim 1, wherein the first inclined surface is configured to define an application direction of a grasping force when the first inclined surface is grasped by the user toward the second surface.

3. The endoscope according to claim 1, wherein the second inclined surface is configured to define an application direction of a grasping force when the second inclined surface is grasped by the user toward the second surface.

4. The endoscope according to claim 1, wherein the first inclined surface is continuous with the ridge of the protruding portion.

5. The endoscope according to claim 1, wherein the second inclined surface is continuous with the ridge of the protruding portion.

6. The endoscope according to claim 1, wherein a first imaginary line directed to the second surface in a direction opposite to a normal line to the first inclined surface is configured to cross the second surface.

7. The endoscope according to claim 6, wherein the first imaginary line extends from a central position of the first inclined surface along a width direction intersecting the longitudinal direction.

8. The endoscope according to claim 1, wherein a second imaginary line directed to the second surface in a direction opposite to a normal line to the second inclined surface is configured to cross the second surface.

9. The endoscope according to claim 8, wherein the second imaginary line extends from a central position of the second inclined surface along a width direction intersecting the longitudinal direction.

10. The endoscope according to claim 1, wherein an edge portion formed between the second inclined surface and the side surface is disposed closer to the second surface than the first surface.

11. The endoscope according to claim 1, wherein a width of the second inclined surface is greater than a width of the first inclined surface.

12. The endoscope according to claim 1, wherein:
    the first surface has a flat portion, and
    the second inclined surface and the flat portion of the first surface form an obtuse angle.

* * * * *